(12) United States Patent
Young

(10) Patent No.: US 7,740,632 B2
(45) Date of Patent: Jun. 22, 2010

(54) VIBRATORY SYRINGE APPARATUS AND IN VIVO DELIVERY METHOD

(75) Inventor: Christopher S. Young, South Kent, CT (US)

(73) Assignee: ISPG, Inc., New Milford, CT (US)

( * ) Notice: Subject to any disclaimer, the term of this patent is extended or adjusted under 35 U.S.C. 154(b) by 292 days.

(21) Appl. No.: 11/820,536

(22) Filed: Jun. 20, 2007

(65) Prior Publication Data
US 2008/0319446 A1 Dec. 25, 2008

(51) Int. Cl.
*A61B 17/58* (2006.01)
*A61B 17/60* (2006.01)
*A61F 2/00* (2006.01)

(52) U.S. Cl. .......................................... 606/93; 606/92

(58) Field of Classification Search ............ 128/DIG. 1; 222/36, 161, 198; 248/562, 610, 638; 433/88–89, 433/103, 114, 117–118; 604/22, 187; 606/92–94, 606/169
See application file for complete search history.

(56) References Cited

U.S. PATENT DOCUMENTS

| | | | |
|---|---|---|---|
| 3,308,823 A * | 3/1967 | Peterson | 604/47 |
| 3,811,442 A * | 5/1974 | Maroth | 604/188 |
| 5,151,030 A * | 9/1992 | Comeaux | 433/118 |
| 5,181,907 A * | 1/1993 | Becker | 604/22 |
| 5,647,851 A * | 7/1997 | Pokras | 604/131 |
| 6,083,229 A * | 7/2000 | Constantz et al. | 606/92 |
| 6,602,229 B2 * | 8/2003 | Coss | 604/187 |
| 6,852,095 B1 * | 2/2005 | Ray | 604/93.01 |
| 7,252,672 B2 * | 8/2007 | Yetkinler et al. | 606/92 |
| 2005/0070914 A1 * | 3/2005 | Constantz et al. | 606/92 |
| 2007/0299453 A1 * | 12/2007 | Constantz et al. | 606/92 |
| 2008/0200916 A1 * | 8/2008 | Murphy | 606/94 |

* cited by examiner

*Primary Examiner*—Thomas C Barrett
*Assistant Examiner*—Larry E Waggle, Jr.
(74) *Attorney, Agent, or Firm*—Alix, Yale & Ristas, LLP

(57) ABSTRACT

An apparatus and a method configured for the efficient delivery of a viscous material, such as bone cement, to a surgical site are described. A housing removably receives a large gauge syringe which is filled with the viscous material. The apparatus is a syringe-type assembly that uses at least one vibrating motor together with a plunger rod assembly. The method employs the continuous application of vibrational forces to the central barrel portion of the apparatus during the time that the viscous material is being delivered and/or applied in vivo. The vibration to the central barrel portion increases the tendency of the viscous material to flow thereby making delivery of such materials easier and more efficient.

17 Claims, 4 Drawing Sheets

VIBRATORY SYRINGE APPARATUS AND IN VIVO DELIVERY METHOD

FIELD OF THE TECHNOLOGY

This application relates generally to an apparatus and method for the delivery of highly viscous materials to a surgical site, and more particularly, to a syringe-like device for the in vivo application of bone cement.

BACKGROUND

Age, injury, trauma, and disease can cause degenerative changes in both the joints and bones of the body. At some point, these degenerative changes can become so advanced and/or debilitating that it becomes necessary to replace a damaged joint with a prosthetic device. In such cases, bone cement is often used to secure the prosthetic device to the natural bone. For those suffering from severer osteoporosis, procedures such as vertebroplasty and kyphoplasty use bone cement to stabilize and/or build up the vertebral bodies that have been weakened by compression fractures. These procedures can help prevent further fracturing of the vertebral bodies as well as relieve the pain caused by existing fractures.

When referring to bone cement it should be understood that bone cement includes any type of surgical cement used in any type of surgical procedure including: resorbable cement, bone graft material, bone substitute, bone filler or any other biologically compatible mixture that is highly viscous.

Bone cement is primarily a two component material, the first component being a powder and the other being a liquid. The cement may also include additional ingredients such as stabilizers, one or more antibiotics, contrast agent(s), and/or colorants. Typically, the powdered component is comprised of polymethylmethacrylate (PMMA) which copolymerizes with the liquid component, methylmethacrylate (MMA), upon mixing. The polymerization process can be divided into four different phases: mixing, waiting, working, and setting.

The mixing phase starts the moment the powder and liquid components come into contact with each other. During this phase the cement is thoroughly mixed to reduce the porosity of the cement and increase its mechanical strength. The mixing phase is also characterized by changes in cement viscosity. At the beginning of mixing, the cement viscosity increases slowly. As the polymerization reaction progresses, however, the cement rapidly becomes increasingly viscous.

In the waiting phase, the cement will achieve a suitable viscosity for delivery to the surgical site. At the beginning of the waiting phase, the cement has a sticky dough-like consistency. However, the optimal consistency for delivering the cement in vivo is attained when the cement loses this sticky quality. Loss of stickiness marks the beginning of the working phase.

In the working phase, the cement is no longer sticky and has a viscosity that is high enough to allow penetration into cancellous bone without leaking into the surrounding tissues. The duration of the working phase is relatively short-lived and, in part, depends upon the type of bone cement being used. For example, low viscosity cements have a relatively short working phase while high viscosity cements have a longer working phase. Cements with a longer working phase typically allow a surgeon more time to apply the cement before the cement enters the setting phase and begins to harden. Regardless of the type of cement used, the finite duration of the working phase necessitates an efficient and precise means for its delivery and application.

In the setting phase, the cement hardens completely and attains its full mechanical strength. Hardening is generally a temperature sensitive process and can be influenced by body temperature, the temperature of the operating room, and the temperature of the bone cement material itself. High viscosity cements are sometimes pre-chilled before mixing, which prolongs the working phase as well as the setting phase. Humidity can also affect the working and setting phases of bone cement.

Considering the time dependent relationship between the optimal viscosity for delivery of the cement to the surgical site and the onset of cement hardening, an efficient, effective and convenient means for delivering bone cement is highly desirable.

SUMMARY

An apparatus and a method are configured for the efficient delivery of a viscous material to a surgical site. To more efficiently deliver a viscous material such as bone cement to a surgical site, the present apparatus and method employs a syringe-type assembly where vibrational forces are applied to the central barrel portion during the time that the viscous material is being delivered and/or applied in vivo. The vibration to the central barrel portion increases the tendency of the viscous material to flow, in this case, towards the outlet of the syringe needle.

In one embodiment, the apparatus comprises a housing member with a central portion that is capable of receiving a standard syringe barrel. A large gauge needle is removably connected to the standard syringe barrel. A cut-out window in the central portion of housing member allows for viewing though a transparent syringe barrel to ascertain the position of the plunger. The apparatus may include at least one switch to actuate vibrating motors and at least one power supply.

In a preferred embodiment, an apparatus for the delivery of a viscous material includes a plurality of vibrating motors disposed on either side of the central barrel portion.

In another preferred embodiment, an apparatus will have several switches that will separately actuate at least one of the plurality of vibrating motors.

DETAILED DESCRIPTION OF THE PREFERRED EMBODIMENTS

Figure 1:
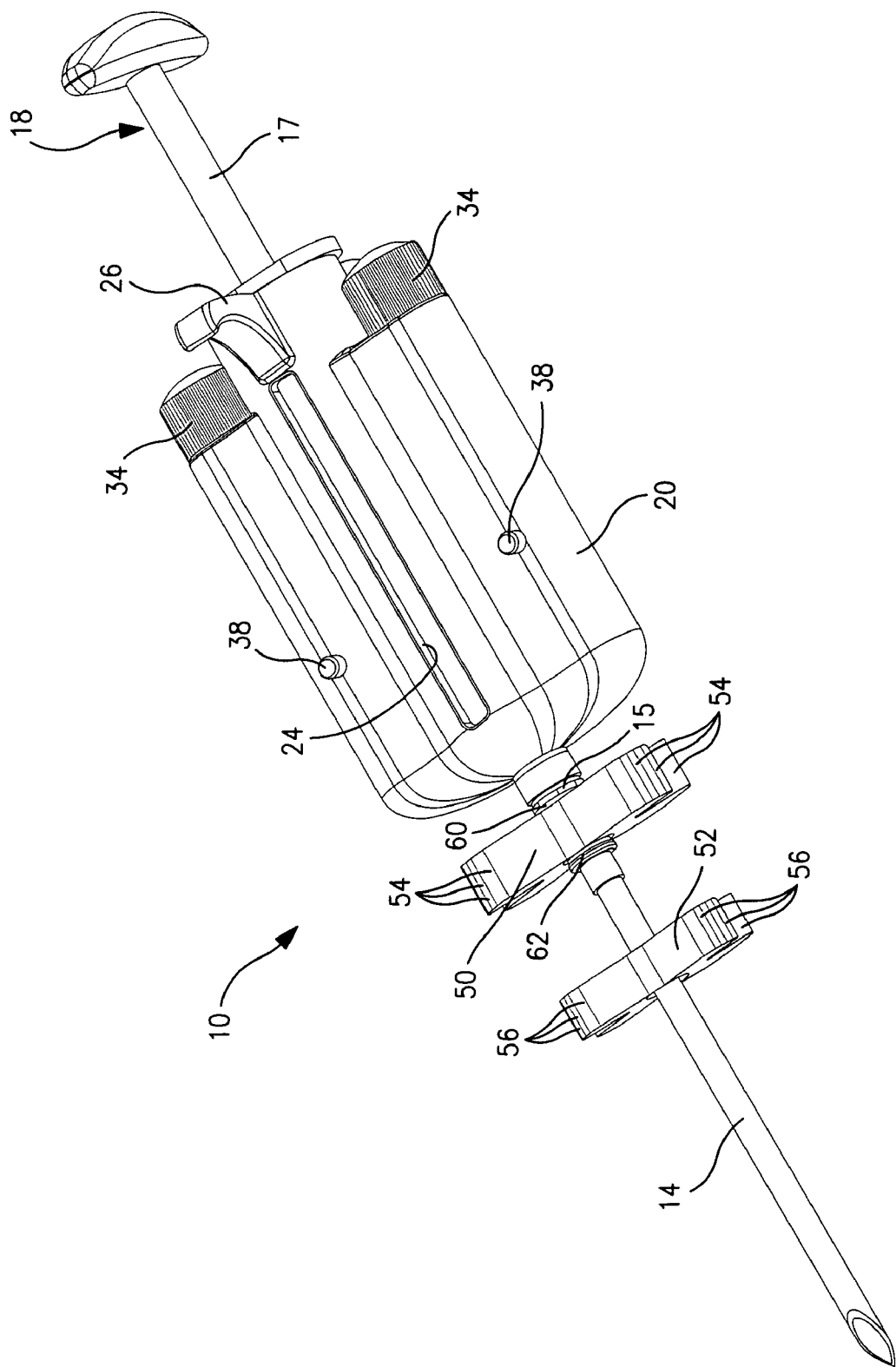
FIG. 1 is a perspective view of an embodiment of the apparatus.
Figure 2:
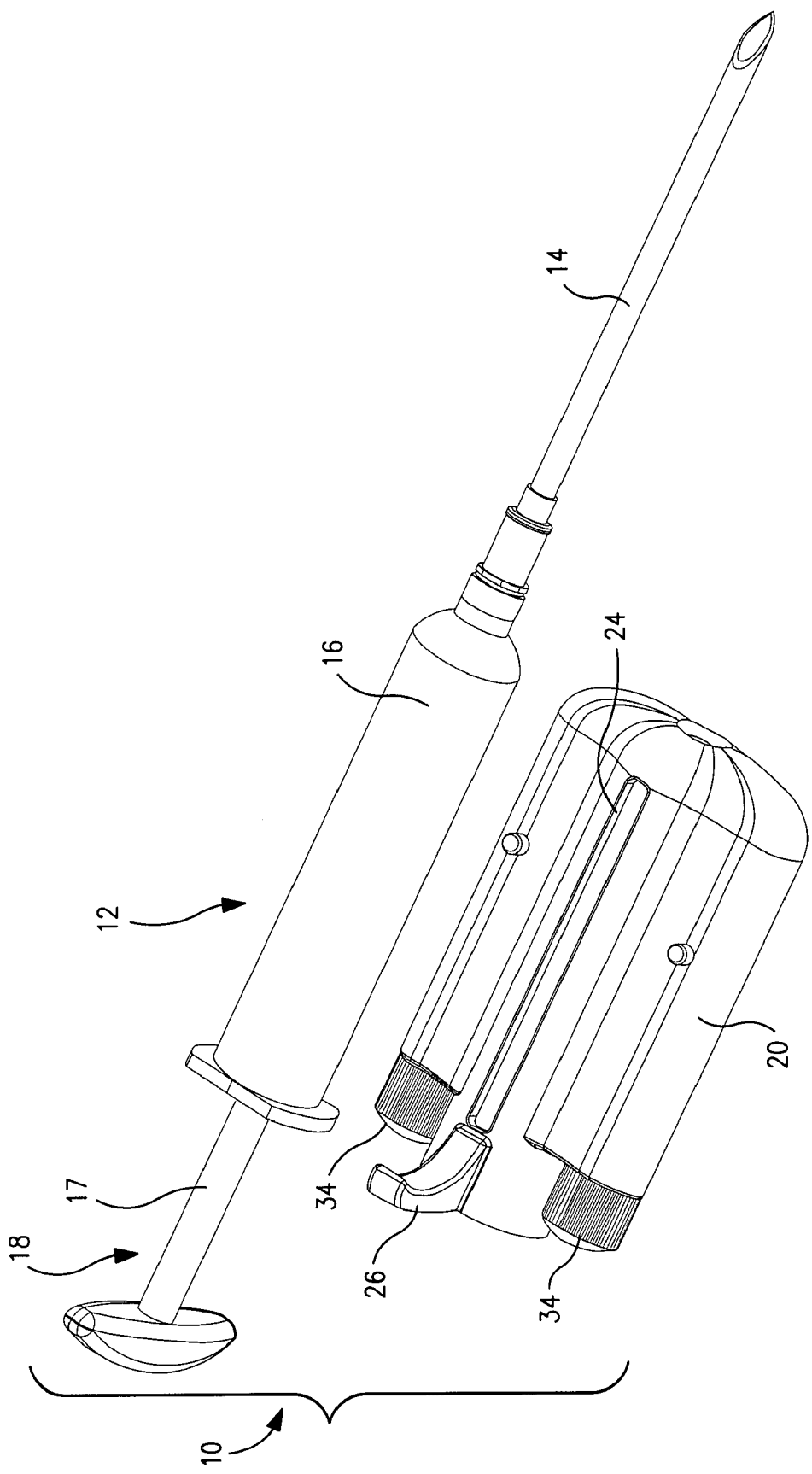
FIG. 2 is a perspective view, portions removed, of the apparatus of FIG. 1 in disassembled form.

With reference to the drawings, wherein like numerals represent like elements throughout the various views, an apparatus for the delivery of viscous materials is generally designated by the numeral 10. The delivery apparatus 10 generally employs a large gauge syringe 12 which includes a large bore needle 14, a barrel 16 and a plunger rod assembly 18 which is specially adapted for more effective and efficient in vivo delivery of viscous materials, such as bone cement, to a surgical site. It should be understood, however, that the delivery apparatus is not limited to the delivery of bone cements but rather its use also extends to, inter alia, biocompatible adhesives and medicines.

Figure 4:
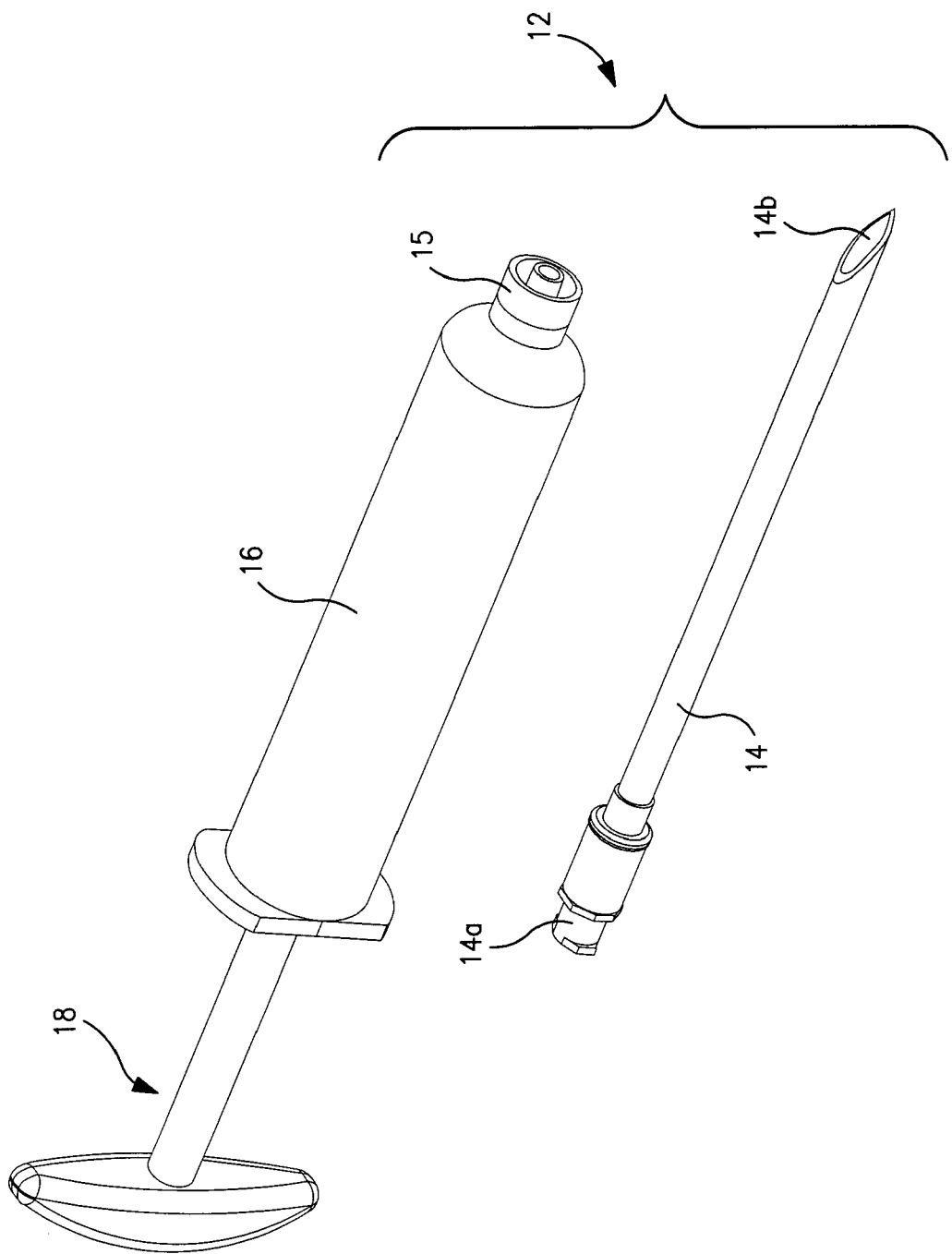
FIG. 4 is a perspective view of the syringe portion of the apparatus of FIG. 3 in disassembled form.

As illustrated in FIG. 4, the syringe 12 includes a large bore needle 14 having a proximal end 14a and a distal tip end 14b. In one preferred embodiment, needle 14 is a 7 gauge needle. The proximal end of the needle 14a is removably connected to a luer connector 15 of a standard syringe barrel 16 (20 ml barrel). The connector 15 may be of any conventional design used in standard medical practice, such as a hub having a luer lock or a thread lock for the attachment of syringes or other medical devices that require the attachment of a needle.

The delivery apparatus 10 includes a contoured housing 20 which generally mounts the principal components such as barrel 16.

The housing 20 has a central barrel-like receiver 22 with an outlet 23. The central receiver 22 is designed to efficiently receive and hold a standard plastic or glass syringe barrel, such as barrel 16. If more adhesive is required during a procedure, the surgeon can simply remove the needle 14 from the standard syringe barrel 16, and then remove the standard syringe barrel and plunger from the main vibration housing 20. Next, the surgeon would reload the main vibration housing with a full syringe barrel and plunger assembly, and reattach the needle. Upon loading of the syringe 12, the receiver 22 is coaxial to the needle 14 which extends axially from the housing and plunger rod assembly 18. The barrel 16 is adapted to receive a predetermined volume of material. Material within the barrel portion 16 is advanced through the needle 14 by the actuation of the plunger rod assembly 18.

In one embodiment, the central portion of receiver 22 of the housing 20 features a viewing window 24. Preferably, the viewing window 24 is a cut-out portion of the receiver. Alternatively, the window 24 may be made from a clear plastic material, which allows the user to observe the contents of the syringe barrel 16 which is also transparent. In a preferred embodiment, the housing is about 3.7 inches in length and about 2.2 inches in width with the central barrel portion having an approximate volume of 20.0 milliliters (ml).

A finger flange 26 to facilitate injection of the syringe may integrally project from the housing 20. In another preferred embodiment the central barrel portion may have two finger flanges 26, each protruding from opposite sides of the housing.

Figure 3:
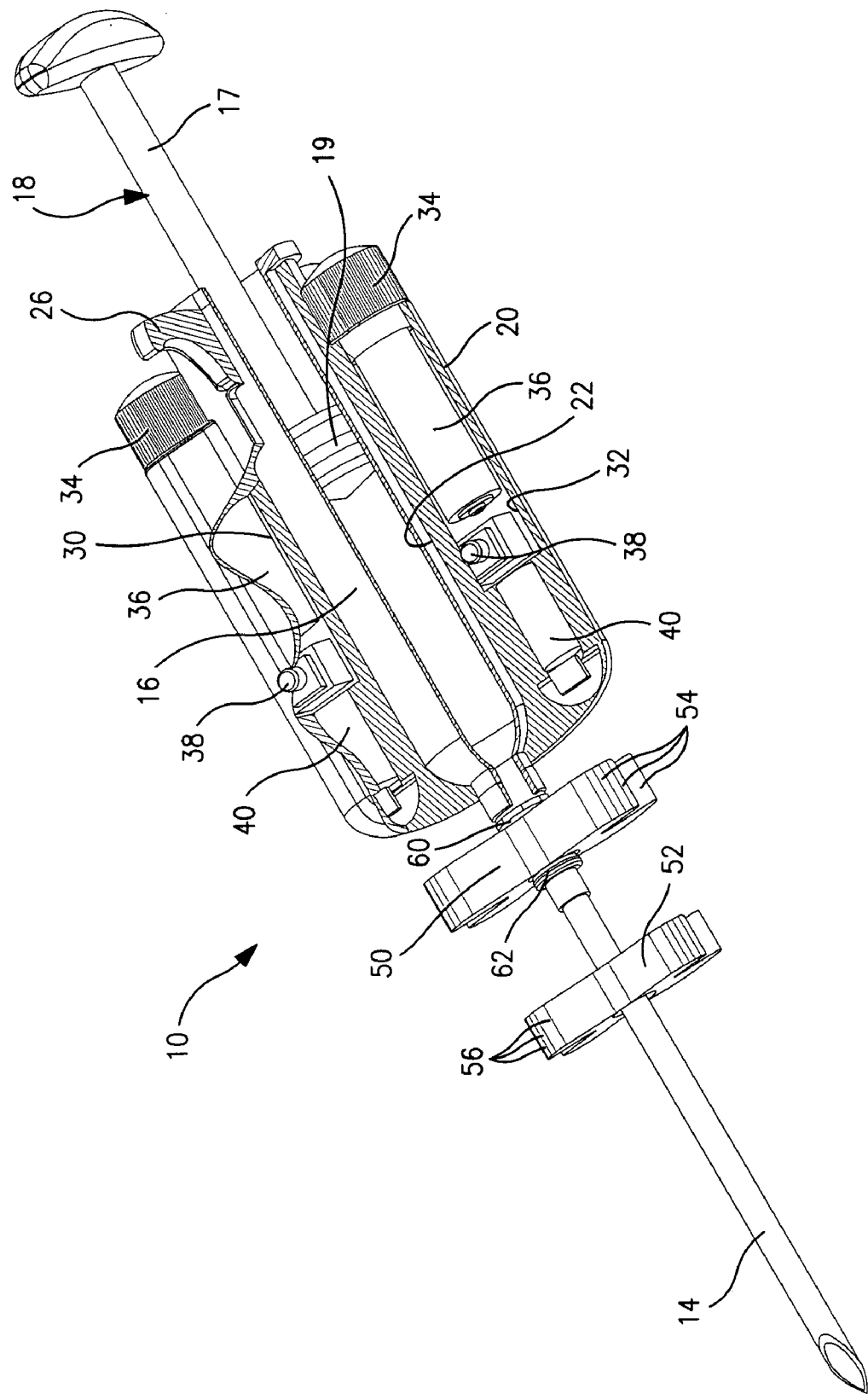
FIG. 3 is a perspective view, partly broken away and partly in section, of the apparatus of FIG. 1.

As best illustrated in FIG. 3, the plunger rod assembly 18 is comprised of a rod 17 and a substantially cylindrical plug 19 disposed within the barrel 16. The cylindrical plug 19 is axially movable along the interior surface of the barrel portion. The cylindrical plug 19 may have a plurality of O-rings or similar means to achieve a sealing fit between the plug and the interior surface of the barrel 16 as the plunger rod is axially displaced. Preferably, the plunger rod assembly is hand operated. Alternatively, the plunger rod assembly may be adapted for use with a mechanical actuator, such as a pneumatic actuator, to assist the user in axially moving the plug 19 within the central barrel to inject viscous material through the needle.

Two side tubular compartments 30 and 32 within the housing may flank the central receiver 22 and extend in generally parallel relationship. Each compartment may have a removable cap 34.

Preferably, each compartment 30, 32 is configured to accommodate a power source 36, a switch 38, and a vibrating motor 40. In another preferred embodiment, the apparatus employs a single vibrating motor. In a preferred embodiment, each power source 36 is a DC battery and each switch 38 is a tactile switch. One exemplary switch is a double-sealed type, B3WN tactile switch manufactured by OMRON Electronics. The switch may be configured or connect with an auxiliary controller to provide a selectively variable speed for the motor.

It should be understood that the placement of the vibrating motor(s) 40 is intended to focus and supply vibration mostly on the front of the internal syringe barrel 16 and where the larger I.D. of the syringe barrel reduces to a smaller I.D. in the vicinity of the connector 18. It is in this area that the cement has a tendency to dam up and block the flow.

A rubber dampener 50 may be placed on the exterior surface of the needle hub to start to reduce vibrations down the length of the needle. In addition, another dampener 52 may be added to the needle shaft, and is capable of sliding along its length. The dampeners 50, 52 include respectively transversely projecting flexible wings 54, 56 or flaps to absorb vibration. Dampener 50 may be axially retained between flanges 60, 62.

Preferably, the vibrating motor 40 is a micro vibration motor that operates at a predetermined speed in the range of between about 5,500 to 11,000 rpm (rotations per minute). It is also preferable that the vibrating motor has an overall length of between about 11 to 25 mm. One exemplary vibrating motor 40 is a coreless cylindrical permanent magnetic micro vibration motor manufactured by JinLong Machinery (part no. 7AL-09WA).

In a preferred embodiment, a vibrating motor operating at a predetermined fixed speed or at a variable speed of, for example, 7,000±1500 rpm increases the tendency of viscous material (not illustrated) within the central syringe barrel to flow, which thereby increases the overall efficiency of the in vivo delivery of the material. In addition, applying vibration to the barrel increases the effectiveness and efficiency of the plunger rod assembly 18 in advancing the material within the barrel portion towards the needle. Also, by applying vibration to the internal syringe barrel loaded with highly viscous material, the resistance pressure to the manual squeezing force between the hand and plunger will be considerably reduced, giving the doctor more control of the delivery of the material.

The delivery apparatus preferably has a plurality of vibrating motors which are each powered by a corresponding power source disposed within the housing 20. A single power source typically energizes a single vibrating motor. Alternatively, a single power source may power the plurality of vibrating motors.

FIG. 3 illustrates one exemplary embodiment of a connection between a power source 36, a switch 38, and a vibrating motor 40. In one embodiment the power source 36 is a AAA battery. Preferably, in an embodiment having a plurality of vibrating motors, each motor may be activated and/or deactivated individually via a dedicated switch. Alternatively, a single switch may actuate a plurality of motors and selectively impose a variable speed for the motors.

The delivery apparatus and particularly the housing 20 is manufactured from durable materials capable of withstanding repeated sterilization.

The vibrating housing receiver is dimensioned to hold standard plastic and glass prefilled/premixed syringes. Naturally, housing receiver 22 may be designed to hold a custom volume premixed/prefilled syringe assembly. The delivery assembly maintains the loaded premixed syringe in a mixed state before and during delivery of the bone cement and facilitates replacement of the syringe during a procedure.

Exemplary embodiments illustrating the apparatus and the method of increasing the efficiency of delivering viscous materials to a surgical site are described for purposes of explanation and are not intended as limitations of the invention herein. Alternative designs and additional modifications may occur to one skilled in the art without departing from the spirit and the scope of the present invention.

What is claimed is:

1. An apparatus for the in vivo delivery of a viscous material, said apparatus comprising:
   an integrated housing having a central longitudinal portion defining a receiver with an outlet and a pair of oppositely disposed, longitudinally extending side portions;
   a syringe comprising a syringe barrel with a front portion which connects with a needle, said barrel received in said receiver and said needle projecting through said outlet, said syringe comprising a plunger assembly received within said barrel and having a plunger rod coaxially slidable within said barrel and a portion of which projects from said housing;
   a plurality of vibrating motors disposed within said housing at said side portions for supplying and focusing vibrational forces on the front portion of the barrel;
   at least one power source electrically connected to at least one of said plurality of vibrating motors; and
   at least one switch for activating said plurality of vibrating motors.

2. The apparatus of claim 1 wherein each of said plurality of vibrating motors is independently activated by at least one switch.

3. The apparatus of claim 2 wherein said at least one switch and at least one of said plurality of vibrating motors are disposed in said side portions and electrically connected to said at least one power source.

4. The apparatus of claim 1 wherein said at least one power source is a DC battery.

5. The apparatus of claim 3 wherein said barrel contains viscous material and at least one vibrating motor is operative to vibrate said barrel at a predetermined speed to inject said viscous material through said needle upon axial displacement of said plunger rod.

6. The apparatus of claim 5 wherein said predetermined speed is between about 5,500 and 11,000 rpm.

7. The apparatus of claim 1 wherein said housing has two compartments, each of which has a vibrating motor, a power source, and a switch.

8. The apparatus of claim 6 wherein said housing has a transparent window along at least a portion adjacent said receiver.

9. The apparatus of claim 1 further comprising a dampener mounted to said needle.

10. The apparatus of claim 9 wherein said dampener is a rubber member comprising at least one wing projecting transversely to said needle.

11. The apparatus of claim 1 wherein at least one of said motors is operated at a selectively variable speed.

12. An apparatus for the in vivo delivery of a viscous material, said apparatus comprising:
    an integrated housing having a plurality of interior parallel longitudinally extending compartments including a central receiver with an outlet;
    a syringe received in said receiver and removably secured therewith, said syringe having a barrel with a front portion which connects with a needle and a plunger, said barrel entirely received in said central receiver with said needle extending beyond said outlet;
    a vibrating motor received in a compartment and operable at a speed for supplying and focusing vibrational forces at the front portion of the barrel;
    a power source electrically connected to said vibrating motor; and
    a switch for activating said vibrating motor.

13. The apparatus of claim 12 wherein said barrel has volume of about 20 ml.

14. The apparatus of claim 12 wherein said speed is between about 5,500 to 11,000 rpm.

15. The apparatus of claim 12 wherein said speed may be selectively varied.

16. The apparatus of claim 12 further comprising a dampener slidably mounted to said needle.

17. The apparatus of claim 12 wherein there are two vibrating motors each received in a said compartment at opposite locations of said receiver.

* * * * *